US009662036B2

(12) United States Patent
Hughes et al.

(10) Patent No.: US 9,662,036 B2
(45) Date of Patent: May 30, 2017

(54) METHOD AND APPARATUS FOR GENERATING A TOMOGRAPHIC IMAGE

(75) Inventors: Timothy Hughes, Erlangen (DE); Tallal Charles Mamisch, Zurich (CH)

(73) Assignees: Siemens Aktiengesellschaft, Munich (DE); Inselspital-Stiftung, Bern (CH)

( * ) Notice: Subject to any disclaimer, the term of this patent is extended or adjusted under 35 U.S.C. 154(b) by 1997 days.

(21) Appl. No.: 12/704,684

(22) Filed: Feb. 12, 2010

(65) Prior Publication Data

US 2010/0208966 A1 Aug. 19, 2010

(30) Foreign Application Priority Data

Feb. 13, 2009 (DE) .................. 10 2009 008 793

(51) Int. Cl.
| | |
|---|---|
| G06K 9/00 | (2006.01) |
| A61B 5/055 | (2006.01) |
| A61B 5/00 | (2006.01) |
| A61B 6/03 | (2006.01) |
| A61B 6/00 | (2006.01) |

(52) U.S. Cl.
CPC ............ A61B 5/055 (2013.01); A61B 5/4514 (2013.01); A61B 6/032 (2013.01); A61B 6/5235 (2013.01)

(58) Field of Classification Search
CPC .................... A61B 6/032; A61B 6/037; G06T 2207/10081; G06T 2207/10072
USPC ................ 378/19, 42, 62, 95; 382/131, 128; 600/410, 443; 424/1.61, 1.65
See application file for complete search history.

(56) References Cited

U.S. PATENT DOCUMENTS

| | | | |
|---|---|---|---|
| 5,187,731 A | 2/1993 | Shimura | |
| 7,103,204 B1 * | 9/2006 | Celler et al. | 382/131 |
| 7,433,444 B2 * | 10/2008 | Baumann et al. | 378/62 |
| 7,559,895 B2 * | 7/2009 | Stetten et al. | 600/443 |
| 7,650,023 B2 * | 1/2010 | Fischer et al. | 382/128 |

(Continued)

OTHER PUBLICATIONS

Susanne Drewsa, Felix Beckmannc, Julia Herzenc, Oliver Brunked, Phil Salmone, Sebastian Friessf, Andres Laibg, Bruno Kollerg, Thomas Hembergerd Magdalena Müller-Gerbla and Bert Müller;Comparative micro computed tomography study of a vertebral body; 2008 SPIE Digital Library; Proc. of SPIE vol. 7078 70780C-1; pp. 1-14.*

(Continued)

*Primary Examiner* — Victoria P Shumate
*Assistant Examiner* — Teresa Williams
(74) *Attorney, Agent, or Firm* — Schiff Hardin LLP

(57) ABSTRACT

In a method for generating a tomographic image, at a first point in time, a first tomographic image is acquired of a layer of a patient and the region of cartilaginous tissue is determined in the first tomographic image. At a later second point in time a second tomographic image is acquired of the layer of the patient and the region of the cartilaginous tissue is determined in the second tomographic image. The tomographic image is generated from the first tomographic image and the second tomographic image, in which every pixel of the tomographic image is assigned a difference value between a corresponding pixel of the first tomographic image and a corresponding pixel of the second tomographic image. The validation number is determined by adding all the pixels in the region of the cartilaginous tissue in the tomographic image.

11 Claims, 3 Drawing Sheets

(56) References Cited

U.S. PATENT DOCUMENTS

| | | | |
|---|---|---|---|
| 7,817,777 B2* | 10/2010 | Baumann | A61B 6/00 378/36 |
| 7,881,768 B2* | 2/2011 | Lang et al. | 600/407 |
| 7,940,893 B2* | 5/2011 | Krauss | 378/98.9 |
| 8,073,099 B2* | 12/2011 | Niu et al. | 378/36 |
| 2006/0239523 A1* | 10/2006 | Stewart | G06T 19/20 382/128 |
| 2007/0153979 A1* | 7/2007 | Baumann et al. | 378/138 |
| 2007/0167801 A1* | 7/2007 | Webler et al. | 600/459 |
| 2007/0189449 A1* | 8/2007 | Baumann et al. | 378/44 |
| 2007/0189455 A1* | 8/2007 | Allison | 378/95 |
| 2008/0139922 A1 | 6/2008 | Pelletier et al. | |
| 2008/0317213 A1 | 12/2008 | Hempel et al. | |
| 2009/0041189 A1* | 2/2009 | Allison | 378/95 |
| 2009/0092227 A1 | 4/2009 | David et al. | |
| 2009/0154640 A1* | 6/2009 | Baumann et al. | 378/19 |
| 2009/0304582 A1* | 12/2009 | Rousso | A61B 5/02755 424/1.61 |

OTHER PUBLICATIONS

Paola Coan, Ph.D.,1 Juergen Mollenhauer, Ph.D., D.Sc.,2,4 Andreas Wagner, M.D.,3 Carol Muehleman, Ph.D.,4 and Alberto Bravin, Ph.D.1; Analyzer-based imaging technique in tomography of cartilage and metal implants: a study at the ESRF; US National Library of Health, Published online Jun. 26, 2008. doi: 10.1016/j.ejrad. 2008.04.036, pp. 1-17.*

"Computer-Aided Method for Quantification of Cartilage Thickness and Volume Changes Using MRI: Validation Study Using a Synthetic Model", Kauffmann et al., IEEE Trans. on Biomedical Engineering, vol. 50, No. 8 (2003) pp. 978-988.

* cited by examiner

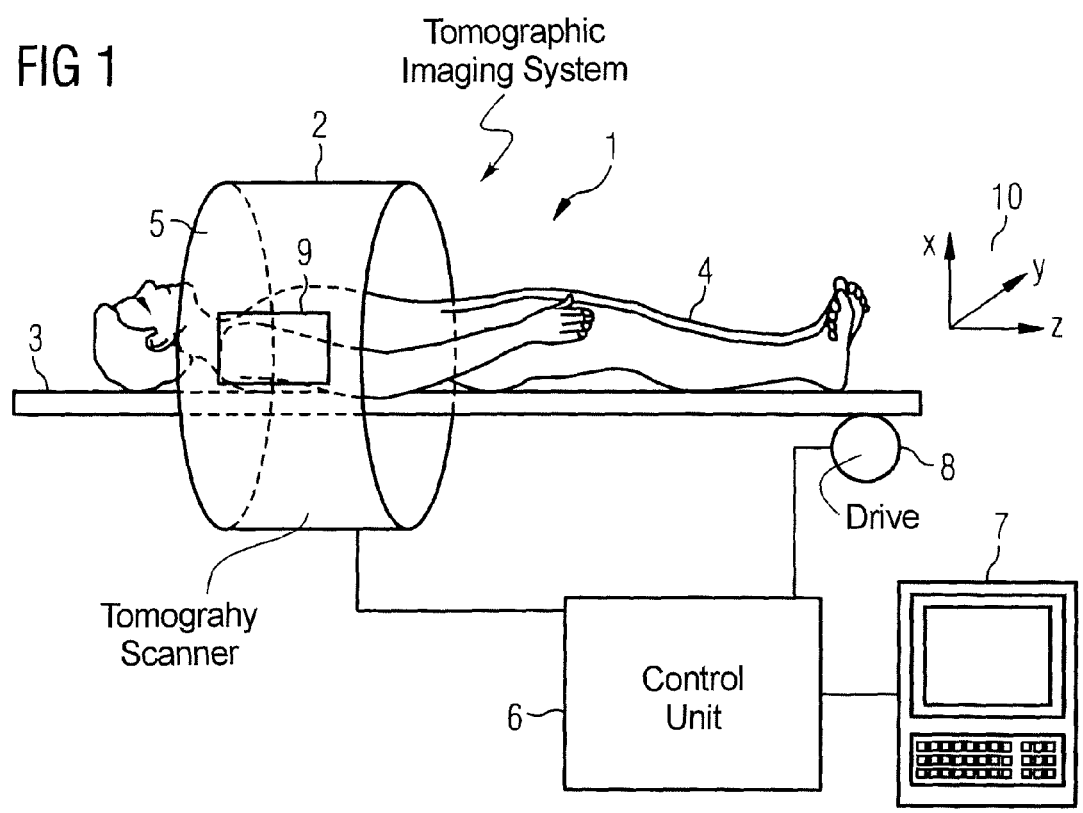

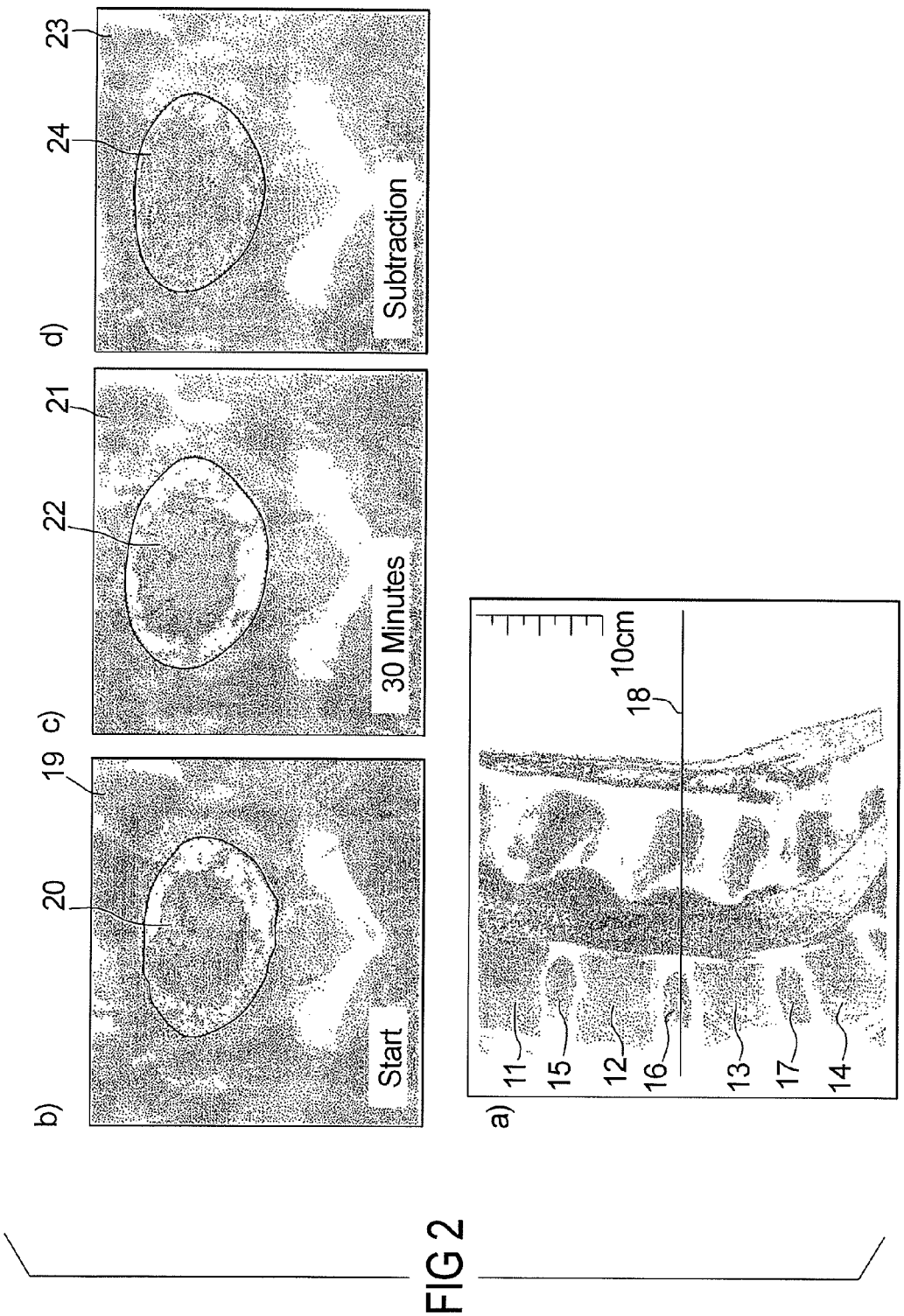

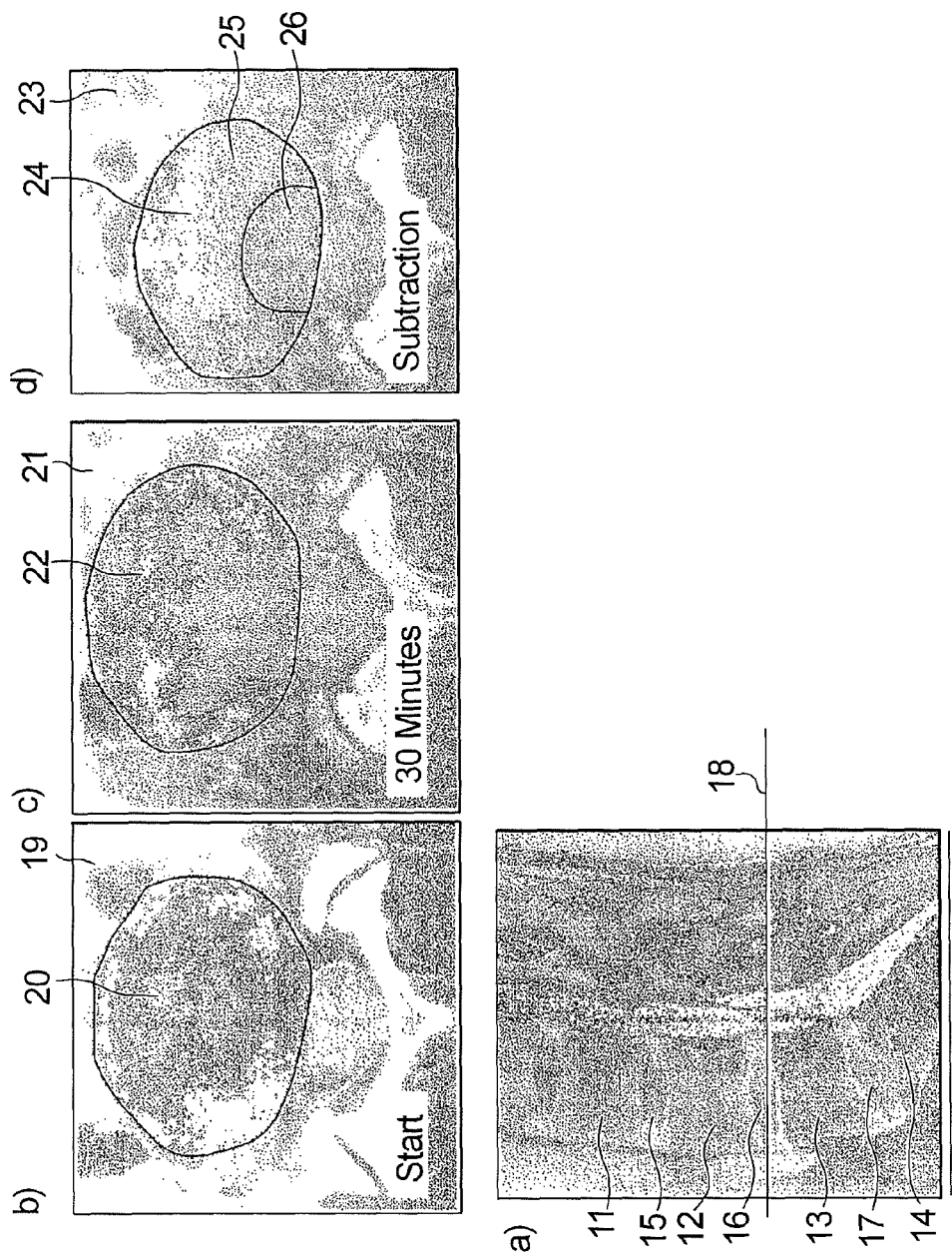

METHOD AND APPARATUS FOR GENERATING A TOMOGRAPHIC IMAGE

BACKGROUND OF THE INVENTION

Field of the Invention

The present invention concerns a method to generate a tomographic image, particularly in a magnetic resonance tomography examination or a computed tomography examination, and especially for generating a tomographic image of cartilaginous tissue.

Description of the Prior Art

Joint pain and particularly back pain, for example in the neck, chest and lumbar region, are a main cause for incapacity to work and occupational disability in our society. Millions of people are affected by it, resulting in a loss of working hours and limitations in activity. The major problems are the current limitations in diagnosis of primarily the biomechanical structures and functions of the intervertebral discs. There is a high rate of up to 80% of patients being incorrectly diagnosed with having back pain although they are really without pain symptoms and patients being incorrectly diagnosed with having no back pain although they really do have back pain. For this reason physicians need to be supported in order to be able to improve their diagnosis and a corresponding therapy.

At present this problem is solved in a purely symptomatic context. The primary elements of the therapeutic concept involve the subjective degree of pain and neurological symptoms, up to complete paresis. Because of this symptom-based diagnosis and a lack of objective parameters to classify an illness and a corresponding therapy, the literature describes a variety of therapy concepts with different results. An image-based diagnosis using magnetic resonance imaging and computer tomography is a common aid to confirm and describe more precisely a symptom-based diagnosis, but because of the high rate of false positive and false negative diagnoses no standardized practical rule can be defined.

SUMMARY OF THE INVENTION

An object of the present invention is to provide improved aids which can assist a physician in his diagnosis of joint pain and back pain.

According to the present invention a method is provided for generating a tomographic image, which is subsequently also called a sequence tomography. At a first point in time during the method, a first tomographic image is acquired of a layer of a patient, and the region of cartilaginous tissue is determined in the first tomographic image. At a second point in time, for example 20 to 40 minutes later, preferably 30 minutes later than the first point in time, a second tomographic image is acquired of the layer of the patient and the region of the cartilaginous tissue is determined in the second tomographic image. The sequence tomography, which is to be shown to the physician, is generated by automatically assigning, to each pixel of this sequence tomography, a difference value between a corresponding pixel of the first tomographic image and a corresponding pixel of the second tomographic image. Furthermore, a validation number is automatically determined by adding all the pixels of the sequence tomography in the region of the cartilaginous tissue. The sequence tomography can be indicated to the treating physician, for example, on a display device together with the validation number for the diagnosis of the cartilaginous tissue. Additionally, the validation number can be nominated onto the size of the region of cartilaginous tissue.

The recordings of the first and the second tomographic image, which are separated by the duration of time between the first point in time and the second point in time, lead to different measurement results because of a difference in the mechanical load of, for example, the spine or a joint of the patient. Accordingly, the sequence tomography shows various effects of the different mechanical loads in individual regions of the cartilaginous tissue or the intervertebral disc. Therefore the sequence tomography can provide additional qualitative information, for example, to indicate the direction of a possible herniated disc. The validation number can be used to indicate the state of health of the intervertebral disc or of the cartilaginous tissue. It has been found that low values indicate a healthy intervertebral disc. Further qualitative information can be used to predict a region of a possible cartilage tear.

According to a further embodiment, the first tomographic image and the second tomographic image are aligned to each other before the sequence tomography is generated. Since the patient may have moved between the periods of recording the two images, the alignment of both of the tomographic images with respect to one another ensures that the region of the cartilaginous tissue in the sequence tomography can be exactly deducted from each other. An alignment of the two tomographic images with respect to each other can be done automatically in a simple manner by using means that are known in image processing. Determining the region of the cartilaginous tissue can also be automatically performed in a simple manner by using means known in image processing.

According to a further embodiment, the layer essentially proceeds perpendicularly to the longitudinal axis of the patient and the cartilaginous tissue encompasses an intervertebral disc of the patient. Since illnesses of the intervertebral disc are a frequent cause for back pain, an examination of this cartilaginous tissue is especially advantageous to treat back pain.

According to a further embodiment, the first tomographic image and the second tomographic image are recorded at different physical stresses of the patient. For example, the first tomographic image can be acquired after the patient stood or sat for a longer period of time, for example half an hour, and a second tomographic image can be acquired after the patient had been lying for the time between the first point in time and the second point in time. A shift of physical stresses results in different measurements of the cartilaginous tissue in the first and the second tomographic image. Equal and slight variations between both tomographic images generally point to a healthy cartilaginous tissue, whereas a major change, especially a major partial change of the cartilaginous tissue between both tomographic images points to a diseased cartilaginous tissue.

According to a further embodiment, the first tomographic image and the second tomographic image can be acquired by magnetic resonance tomography or by computed tomography. Thus the method described above is very suitable for use in a variety of common hospital examination devices.

The present invention also provides a magnetic resonance imaging apparatus for the purpose of generating a tomographic image. The magnetic resonance imaging scanner includes a control unit to operate a scanner of the magnetic resonance imaging apparatus and to receive signals that are acquired by the scanner, and an evaluation device that analyzes the signals and generates a magnetic resonance tomographic image. The control unit of the magnetic resonance imaging apparatus is configured to operate the scanner to acquire, at a first point in time, a first tomographic image of a layer of a patient and to determine a region of a cartilaginous tissue in the first tomographic image. At a second point in time, the magnetic resonance imaging scanner takes a second tomographic image of the layer of a patient and determines the region of the cartilaginous tissue in the second tomographic image. Then the magnetic resonance imaging scanner generates the sequence tomography in which the magnetic resonance imaging scanner assigns each pixel of the sequence tomography a difference value between a corresponding pixel of the first tomographic image and a corresponding pixel of a second tomographic image. Finally the magnetic resonance imaging scanner adds up all the pixels of the sequence tomography in the region of the cartilaginous tissue to thereby determine a validation number. Therefore the magnetic resonance imaging scanner is suitable to perform the process described above. The magnetic resonance imaging scanner thus provides the physician with valuable information to diagnose cartilage diseases, especially disc diseases.

According to the preset invention, a computed tomography system is also provided to generate a tomographic image. The computed tomography system includes a control unit that operates a computed tomography scanner, and receives signals acquired by the scanner, and an evaluation device that analyzes the signals, and that generates a computed tomography tomographic image. The computed tomography system is configured to operate the computed tomography scanner to acquire, at a first point in time, a first tomographic image of a layer of a patient and determines a region of a cartilaginous tissue in the first tomographic image. At a second point in time, the computed tomography system acquires a second tomographic image of the layer of the patient and then again the region of the cartilaginous tissue is determined in the second tomographic image. Finally the sequence tomography is generated as the computed tomography system assigns each pixel of the sequence tomography a difference value between a corresponding pixel of the first tomographic image and a corresponding pixel of the second tomographic image. A validation number is determined by adding all pixels of the sequence tomography in the region of the cartilaginous tissue. Just like the magnetic resonance imaging system described above, the computed tomography system is suitable to perform the procedure described above and thus provides the physician with valuable information to diagnose cartilage disease and disc disease.

According to the present invention a computer-readable medium encoded with programming instructions that can be loaded into the memory of a programmable controller of a magnetic resonance imaging scanner or computer tomography scanner. All the aforementioned embodiments of the present invention-based processes can be performed with the processor means of the programming instructions.

The electronically readable data can be a CD or DVD.

BRIEF DESCRIPTION OF THE DRAWINGS

FIG. 1 schematically illustrates a magnetic resonance imaging system according to an embodiment of the present invention.

FIGS. 2a-2c show tomographic images of a healthy intervertebral disc and FIG. 2d shows a tomographic image of the healthy intervertebral disc, determined according to the present invention.

FIGS. 3a-3c show tomographic images of a diseased intervertebral disc and FIG. 3d shows a tomographic image of the diseased intervertebral disc, determined according to the present invention.

DESCRIPTION OF THE PREFERRED EMBODIMENTS

FIG. 1 shows a tomographic imaging system 1, which includes the actual scanner 2, an examination table 3 for a patient 4 that is located in an opening 5 of the scanner 2, a control unit 6, an evaluation device 7, and a drive unit 8. The scanner 2 may be a magnetic resonance scanner or a computed tomography scanner. The control unit 6 operates the scanner 2 and receives signals from the scanner 2, which are acquired by the scanner 2. Furthermore, the control unit 6 controls the drive unit 8, to move the examination table 3, together with the patient 4, along a direction z through the opening 5 of the scanner 2. The evaluation device 7 evaluates the signals acquired by the scanner 2 to generate a magnetic resonance image (MR image). The evaluation device 7, for example, is a computer system with a monitor, a keyboard, a pointer input device, such as a mouse, and a data carrier, onto which electronically readable control information is stored. It is designed to perform the following method to generate a tomographic image during a examination, by use of the data carrier.

In the method, the patient 4 is arranged onto the examination table 3 and, with the control unit 6 and the drive unit 8, the patient 4 is moved in the scanner 2 so that the examination area of the patient 4 is located in the scanner 2 in a so-called Field of View, which means an examining area. Measurement data can be acquired through a suitable controller of the scanner 2 with the control unit 6, which can be further processed in the evaluation device 7 into so called tomographic images.

FIG. 2a shows such a tomographic image of a region of the spine of the patient 4. The tomographic image represented in FIG. 2a extends in the x and z directions in the coordinate system 10 represented in FIG. 1. Among other things, FIG. 2a shows multiple vertebral bodies 11-14 and intermediary intervertebral discs 15-17. FIG. 2a also depicts a section axis 18, along which subsequently further tomographic images are acquired in the x/y plane.

At a first point in time, a first tomographic image 19 of the layer 18 of the patient 4 is recorded. FIG. 2b shows the result of this tomographic image 19. In this first tomographic image 19 a region 2 is determined, which represents the intervertebral disc 16. After 30 minutes, a second tomographic image is acquired of the same layer 18 of the patient 4. The result of this second tomographic image 21 is represented in FIG. 2c. The region 22 of the intervertebral disc 16 is also determined in this second tomographic image 21. Since it is possible that the patient 4 has moved in the time between the first tomographic image 19 and the second tomographic image 21, both the tomographic images 19 and 21 will be aligned such that the regions 20 and 22 of the intervertebral disc 16 cover each other. Then a further tomographic image 23 is generated on a pixel basis, a so-called sequence tomography, by assigning a difference value to each pixel of the tomographic image 23, between a corresponding pixel of the first tomographic image 19 and a respective pixel of the second tomographic image 21. This sequence tomography 23 is represented in FIG. 2d. The regions 20 and 22 of the first and second tomographic image 19 or 21, which cover each other, result in the region 24 of the sequence tomographic 23, representing the intervertebral disc 16. An evaluation number is furthermore determined in the sequence tomography 23 by adding all pixels which are in the region 24. For standardization purposes, the thus obtained evaluation number can be divided, for example, by the number of pixels in the region 24.

The physician can diagnose the condition of the intervertebral disc 16 by means of the sequence tomography 23 and the validation number thus obtained. The differences of the measured intervertebral disc structures in both tomographic images 19 and 21 result from the fact that the first tomographic image 19 shows the intervertebral disc in a condition in which the disc has been strained, for example, after sitting or standing. However, the second tomographic image 21 shows the intervertebral disc 16 in a condition which was not strained for an extended period of time, because the patient was lying, for example, on the examination table 3 for 30 minutes between the two tomographic images. By means of the sequence tomography 23, the physician can determine if specific regions of the intervertebral disc 16 are subject to a greater change in the course of the examination, or if the entire region of the intervertebral disc 16 has equally changed. Examinations have shown that, during the above-mentioned change from the strained condition to the unstrained condition, a healthy intervertebral disc basically shows an equal and basically small change across the entire cross-section of the intervertebral disc. Accordingly, in a healthy intervertebral disc, the region 24 of the intervertebral disc 16 in the sequence tomography 23 is homogeneous and the validation number thus determined is low. The sectional images represented in FIGS. 2a-2d depict a healthy intervertebral disc, whereas the discussed tomographic images of FIGS. 3a-3d represent a diseased intervertebral disc.

FIG. 3a shows a sectional view of a section of a spine of a patient 4 in an x/y plane that is comparable to FIG. 2a. The spine consists of multiple vertebral bodies 11-14 and intermediary intervertebral discs 15-17. The intervertebral disc 16 is recorded along the x/y plane 18 at a first point in time and 30 minutes later at a second point in time. FIGS. 3b and 3c show both of the recorded tomographic images 19 or 21.

As described in connection with FIGS. 2b and 2c, the region 20 or 22 of the intervertebral disc 16 is determined in the first tomographic image 19 and the second tomographic image 21 of FIG. 3b or 3c respectively. This determination can be made, for example, by corresponding image processing software with the aid of anatomical knowledge in the evaluation device 7. Alternatively, a physician can manually determine the regions 20 and 22 by marking the regions 20 or 22, for example, on a monitor of the evaluation device 7 by means of an appropriate pointing device, as, for example, a mouse or an electronic stylus. With the regions 20 and 22 determined, both tomographic images 19 and 21 are aligned to each other so that a sequence tomography 23 can be generated by establishing difference values between the corresponding pixels of the first tomographic image 19 and the second tomographic image 21. A region 24, which represents the intervertebral disc 16 in the sequence tomography 23, can be determined directly from the regions 20 and 22 aligned to each other. Finally, a validation number is determined by adding all the pixels in the region 24 of the sequence tomography 23. The validation number can additionally be standardized by being divided by the number of pixels in the region 24. FIG. 3d shows the sequence tomography 23.

The examined intervertebral disc 16 shown in FIGS. 3a-3d is a diseased intervertebral disc which is evident to the physician by the generated sequence tomography 23 in FIG. 3d and the validation number determined therefrom. The intervertebral disc region 24 of the sequence tomography 23 is inhomogeneous and essentially exhibits two different structural regions 25 and 26 which can be clearly distinguished in the sequence tomography 23. Also, the validation number resulting from the sequence tomography 23 in FIGS. 3a-3d is considerably higher than the corresponding validation number in FIGS. 2a-2d. This also indicated that the intervertebral disc 16 is diseased. Further diagnostic statements, such as, for example, a direction in which a herniated disc can occur, can be easily read from the sequence tomographies in combination with the empirical values that the physician gathers from analyzing the sequence tomographies generated according to the present invention.

The method described above was described in connection with an examination of an intervertebral disc of a patient. However, the present invention is not limited to examinations of intervertebral discs but can be applied to any examination, especially any cartilaginous tissue of the musculoskeletal system of a patient, for example, the cartilage in an ankle, a knee or a hip. Also, depending on the tissue being examined, the time interval between the first tomographic image in a strained condition or shortly after a strained condition and the second tomographic image in an unstrained or for a longer period of time unstrained condition can be arranged differently. For example, suitable intervals between the two tomographic images range between 10 and 60 minutes. Suitable levels to distinguish healthy cartilaginous tissue from diseased cartilaginous tissue by means of the validation number can be empirically determined and depend on the type of system used to record the tomographic images and the type of tissue being examined (intervertebral disc, cartilage in the knee, cartilage in the hip, etc.). Besides the aforementioned summaries of all the pixels in the region of the cartilaginous tissue, other mathematical connections can also be used to determine the validation number, as, for example determining a variation or an average deviation of the pixels in the region of the cartilaginous tissue.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a tomographic image, comprising the steps of:

placing a patient in a tomographic data acquisition unit and operating the tomographic data acquisition unit to acquire tomographic data representing a first tomographic image of a layer, containing cartilaginous tissue of the patient at a first point in time after subjecting said cartilaginous tissue of the patient to a physical strain at which said cartilaginous tissue still exhibits an effect of said physical strain, said first tomographic image being comprised of pixels;

determining a region of said cartilaginous tissue in said first tomographic image;

operating said tomographic data acquisition unit to acquire tomographic data representing a second tomographic image of the layer of the patient at a second point in time following said first point in time, at which said effect of said physical strain is no longer exhibited by said cartilaginous tissue, said second tomographic image being comprised of pixels;

determining said region of said cartilaginous tissue in said second tomographic image;

generating a diagnostic tomographic image, comprised of pixels, by assigning, to each pixel in said diagnostic tomographic image, a difference value between a corresponding pixel of said first tomographic image and a corresponding pixel of said second tomographic image; and in a processor, automatically determining a validation number by adding respective values of all pixels in said region of cartilaginous tissue in said diagnostic tomographic image, and emitting said validation number from said processor as an indicator of a degree of pathology of said cartilaginous tissue.

2. A method as claimed in claim 1 comprising bringing said second tomographic image into registration with said first tomographic image before generating said diagnostic tomographic image.

3. A method as claimed in claim 1 comprising acquiring said tomographic data representing said second tomographic image at said second point in time that follows said first point in time by a duration in a range between 20 and 40 minutes.

4. A method as claimed in claim 1 wherein the patient has a longitudinal axis, and selecting said layer as a layer proceeding perpendicularly to said longitudinal axis with said cartilaginous tissue therein encompassing an intervertebral disc of the patient.

5. A method as claimed in claim 1 comprising placing said patient in different degrees of physical strain in said layer respectively at said first and second points in time.

6. A method as claimed in claim 1 comprising acquiring said first and second tomographic images by placing the patient in a magnetic resonance scanner, as said tomographic data acquisition unit.

7. A method as claimed in claim 1 comprising acquiring said first and second tomographic images by placing the patient in a computed tomography scanner, as said tomographic data acquisition unit.

8. An apparatus for generating a tomographic image, comprising:

a tomographic data acquisition unit configured to receive a patient therein, said patient containing cartilaginous tissue has been subjected to a physical strain;

a control unit configured to operate the tomographic data acquisition unit to acquire tomographic data representing a first tomographic image of a layer, containing said cartilaginous tissue, of the patient at a first point in time after subjecting cartilaginous tissue of the patient to the physical strain, at which said cartilaginous tissue still exhibits an effect of said physical strain, said first tomographic image being comprised of pixels;

a processor configured to automatically determine a region of said cartilaginous tissue in said first tomographic image;

said control unit being configured to operate said tomographic data acquisition unit to acquire tomographic data representing a second tomographic image of the layer of the patient at a second point in time, following said first point in time, at which said effect of said physical strain is no longer exhibited by said cartilaginous tissue, said second tomographic image being comprised of pixels;

said processor being configured to automatically determine said region of said cartilaginous tissue in said second tomographic image;

said processor being configured to generate a diagnostic tomographic image, comprised of pixels, by assigning, to each pixel in said diagnostic tomographic image, a difference value between a corresponding pixel of said first tomographic image and a corresponding pixel of said second tomographic image; and said processor being configured to automatically determine a validation number by adding respective values of all pixels in said region of cartilaginous tissue in said diagnostic tomographic image, and to emit said validation number from said processor as an indicator of a degree of pathology of said cartilaginous tissue.

9. An apparatus as claimed in claim 8 wherein said tomographic data acquisition unit is a magnetic resonance scanner.

10. An apparatus as claimed in claim 8 wherein said tomographic data acquisition unit is a computed tomography scanner.

11. A non-transitory computer-readable medium encoded with programming instructions, said medium being loadable into a computerized control system that operates a tomographic data acquisition unit to acquire tomographic data from a patient, said patient containing cartilaginous tissue that has been subjected to a physical strain, said programming instructions causing said computerized control system to:

operate the tomographic data acquisition unit to acquire tomographic data representing a first tomographic image of a layer, containing said cartilaginous tissue, of the patient in the tomographic acquisition unit at a first point in time after subjecting cartilaginous tissue of the patient to the physical strain, at which said cartilaginous tissue still exhibits an effect of said physical strain, said first tomographic image being comprised of pixels;

determine a region of said cartilaginous tissue in said first tomographic image;

operate said tomographic data acquisition unit to acquire tomographic data representing a second tomographic image of the layer of the patient in the tomographic acquisition unit at a second point in time following said first point in time, at which said effect of said physical strain is no longer exhibited by said cartilaginous tissue, said second tomographic image being comprised of pixels;

determine said region of said cartilaginous tissue in said second tomographic image;

generate a diagnostic tomographic image, comprised of pixels, by assigning, to each pixel in said diagnostic tomographic image, a difference value between a corresponding pixel of said first tomographic image and a corresponding pixel of said second tomographic image; and automatically determine a validation number by adding respective values of all pixels in said region of cartilaginous tissue in said diagnostic tomographic image, and emitting said validation number from said computerized control system as an indicator of a degree of pathology of said cartilaginous tissue.

* * * * *